United States Patent [19]
Cook et al.

[11] Patent Number: 5,562,740
[45] Date of Patent: Oct. 8, 1996

[54] PROCESS FOR PREPARING REDUCED ODOR AND IMPROVED BRIGHTNESS INDIVIDUALIZED, POLYCARBOXYLIC ACID CROSSLINKED FIBERS

[75] Inventors: Jeffery T. Cook, Cincinatti; Walter D. Daniels, Maineville; Pedro A. Rodriguez, Cincinnati, all of Ohio; Peter A. Graef, Puyallup, Wash.; Clifford R. Bolstad, Federal Way, Wash.; William L. Duncan, Seattle, Wash.

[73] Assignee: The Procter & Gamble Company, Cincinatti, Ohio

[21] Appl. No.: 490,793

[22] Filed: Jun. 15, 1995

[51] Int. Cl.$^6$ .................... D06M 13/192; D21H 11/20
[52] U.S. Cl. ................... 8/120; 8/116.1; 8/107; 8/108.1; 8/109; 8/110; 8/111; 8/115.69; 162/9; 162/157.6
[58] Field of Search ................ 8/120, 116.1, 121, 8/129, 107, 108.1, 109, 110, 111, 115.68, 115.69; 162/157.6, 9, 109, 158

[56] References Cited

U.S. PATENT DOCUMENTS

| | | |
|---|---|---|
| 2,872,280 | 2/1959 | Kindron . |
| 3,526,048 | 9/1970 | Rowland et al. ............... 8/120 |
| 4,298,426 | 11/1981 | Torregrossa et al. . |
| 4,303,470 | 12/1981 | Meredith et al. . |
| 4,409,384 | 10/1983 | Lindsey . |
| 4,624,743 | 11/1986 | Gess . |
| 4,731,161 | 3/1988 | Ehrhardt . |
| 4,734,161 | 3/1988 | Dubreux . |
| 4,804,440 | 2/1989 | Liebergott et al. . |
| 4,820,307 | 4/1989 | Welch et al. ............... 8/120 |
| 4,889,595 | 12/1989 | Herron et al. . |
| 5,137,537 | 8/1992 | Herron et al. ............... 8/120 |
| 5,183,707 | 2/1993 | Herron et al. ............... 428/364 |
| 5,190,563 | 3/1993 | Herron et al. ............... 8/120 |
| 5,199,953 | 4/1993 | Fung et al. ............... 8/120 |
| 5,296,100 | 3/1994 | Devic . |
| 5,366,591 | 11/1994 | Jewell . |

*Primary Examiner*—Prince Willis, Jr.
*Assistant Examiner*—Alan D. Diamond
*Attorney, Agent, or Firm*—Bart S. Hersko; E. Kelly Linman; Jacobus C. Rasser

[57] ABSTRACT

Disclosed is a process for making reduced odor individualized, crosslinked fibers which includes the steps of providing cellulosic fibers, contacting the fibers with a solution containing a $C_2$–$C_9$ polycarboxylic acid crosslinking agent, mechanically separating the fibers into substantially individual form, drying the fibers and reacting the crosslinking agent with the individualized fibers to form intrafiber crosslink bonds. The individualized cellulosic fibers are then contacted with a strong alkaline solution and strong oxidizing agent to reduce the odor and increase the brightness. Preferably, the crosslinking agent is citric acid, and preferably, between about 1.0 weight % and about 12.0 weight % of the crosslinking agent reacts to form the intrafiber crosslink bonds. Preferably, the alkaline solution is an aqueous solution of sodium hydroxide, and preferably, about 0.09 weight % of the sodium hydroxide, on a dry fiber weight basis, is applied to the crosslinked fibers. Preferably, the oxidizing agent is hydrogen peroxide, and preferably, about 0.04 weight % of the hydrogen peroxide, on a dry fiber weight basis, is applied to the crosslinked fiber. The reduced odor individualized, crosslinked fibers are useful in a variety of absorbent structure applications.

21 Claims, No Drawings

PROCESS FOR PREPARING REDUCED ODOR AND IMPROVED BRIGHTNESS INDIVIDUALIZED, POLYCARBOXYLIC ACID CROSSLINKED FIBERS

FIELD OF INVENTION

This invention is concerned with cellulosic fibers having high fluid absorption properties, absorbent structures made from such cellulosic fibers, and processes for making such fibers and structures. More specifically, this invention is concerned with reduced odor and improved brightness individualized, crosslinked cellulosic fibers, processes for making such fibers, and absorbent structures containing cellulosic fibers which are in an individualized, crosslinked form.

BACKGROUND OF THE INVENTION

Fibers crosslinked in substantially individualized form and various methods for making such fibers have been described in the art. The term "individualized, crosslinked fibers", refers to cellulosic fibers that have primarily intrafiber chemical crosslink bonds. That is, the crosslink bonds are primarily between cellulose molecules of a single fiber, rather than between cellulose molecules of separate fibers. Individualized, crosslinked fibers are generally regarded as being useful in absorbent product applications. The fibers themselves and absorbent structures containing individualized, crosslinked fibers generally exhibit an improvement in at least one significant absorbency property relative to conventional, uncrosslinked fibers. Often, the improvement in absorbency is reported in terms of absorbent capacity. Additionally, absorbent structures made from individualized crosslinked fibers generally exhibit increased wet resilience and increased dry resilience relative to absorbent structures made from uncrosslinked fibers. The term "resilience" shall hereinafter refer to the ability of pads made from cellulosic fibers to return toward an expanded original state upon release of a compressional force. Dry resilience specifically refers to the ability of an absorbent structure to expand upon release of compressional force applied while the fibers are in a substantially dry condition. Wet resilience specifically refers to the ability of an absorbent structure to expand upon release of compressional force applied while the fibers are in a moistened condition. For the purposes of this invention and consistency of disclosure, wet resilience shall be observed and reported for an absorbent structure moistened to saturation.

In general, three categories of processes have been reported for making individualized, crosslinked fibers. These processes, described below, are herein referred to as dry crosslinking processes, aqueous solution crosslinking processes, and substantially non-aqueous solution crosslinking processes.

Processes for making individualized, crosslinked fibers with dry crosslinking technology are described in U.S. Pat. No. 3,224,926, L. J. Bernardin, issued Dec. 21, 1965. Individualized, crosslinked fibers are produced by spraying cellulose drylap with crosslinking agent, defiberizing the fibers by mechanical action, and drying the fibers at elevated temperature to effect crosslinking while the fibers are in a substantially individual state. The fibers are inherently crosslinked in an unswollen, collapsed state as a result of being dehydrated prior to crosslinking. Processes as exemplified in U.S. Pat. Nos. 3,224,926, wherein crosslinking is caused to occur while the fibers are in an unswollen, collapsed state, are referred to as processes for making "dry crosslinked" fibers. Dry crosslinked fibers are generally highly stiffened by crosslink bonds, and absorbent structures made therefrom exhibit relatively high wet and dry resilience. Dry crosslinked fibers are further characterized by low fluid retention values (FRV).

Processes for producing aqueous solution crosslinked fibers are disclosed, for example, in U.S. Pat. No. 3,241,553, F. H. Steiger, issued Mar. 22, 1966. Individualized, crosslinked fibers are produced by crosslinking the fibers in an aqueous solution containing a crosslinking agent and a catalyst. Fibers produced in this manner are hereinafter referred to as "aqueous solution crosslinked" fibers. Due to the swelling effect of water on cellulosic fibers, aqueous solution crosslinked fibers are crosslinked while in an uncollapsed, swollen state. Relative to dry crosslinked fibers, aqueous solution crosslinked fibers as disclosed in U.S. Pat. No. 3,241,553 have greater flexibility and less stiffness, and are characterized by higher fluid retention value (FRV). Absorbent structures made from aqueous solution crosslinked fibers exhibit lower wet and dry resilience than structures made from dry crosslinked fibers.

In U.S. Pat. No. 4,035,147, Sangenis et al., issued Jul. 12, 1977, a method is disclosed for producing individualized, crosslinked fibers by contacting dehydrated, nonswollen fibers with crosslinking agent and catalyst in a substantially nonaqueous solution which contains an insufficient amount of water to cause the fibers to swell. Crosslinking occurs while the fibers are in this substantially nonaqueous solution. This type of process shall hereinafter be referred to as a nonaqueous solution crosslinked process; and the fibers thereby produced shall be referred to as nonaqueous solution crosslinked fibers. The nonaqueous solution crosslinked fibers disclosed in U.S. Pat. No. 4,035,147 do not swell even upon extended contact with solutions known to those skilled in the art as swelling reagents. Like dry crosslinked fibers, they are highly stiffened by crosslink bonds, and absorbent structures made therefrom exhibit relatively high wet and dry resilience.

Crosslinked fibers as described above are believed to be useful for lower density absorbent product applications such as diapers and also higher density absorbent product applications such as catamenials. However, such fibers have not provided sufficient absorbency benefits, in view of their detriments and costs, over conventional fibers to result in significant commercial success. In addition, such fibers typically exhibit high objectionable odor and have low fiber brightness.

The use of formaldehyde and various formaldehyde addition products to crosslink cellulosic fibers is known in the art. See, for example, U.S. Pat. No. 3,224,926, Bernardin, issued on Dec. 21, 1965; U.S. Pat. No. 3,241,553, Steiger, issued on Mar. 22, 1966; U.S. Pat. No. 3,932,209, Chatterjee, issued on Jan. 13, 1976; U.S. Pat. No. 4,035,147, Sangenis et al, issued on Jul. 12, 1977; and U.S. Pat. No. 3,756,913, Wodka, issued on Sep. 4, 1973. Unfortunately, the irritating effect of formaldehyde vapor on the eyes and skin is a marked disadvantage of such references. In addition, such crosslinked fibers typically exhibit high objectionable odor and have low fiber brightness. A need is evident for cellulosic fiber crosslinking agents that do not require formaldehyde or its unstable derivatives.

Other references disclose the use of dialdehyde crosslinking agents. See, for example, U.S. Pat. No. 4,689,118, Makoui et al, issued on Aug. 25, 1987; and U.S. Pat. No. 4,822,453, Dean et al, issued on Apr. 18, 1989. The Dean et al reference discloses absorbent structures containing individualized, crosslinked fibers, wherein the crosslinking agent is selected from the group consisting of $C_2$–$C_9$ dialdehydes, with glutaraldehyde being preferred. These references appear to overcome many of the disadvantages associated with formaldehyde and/or formaldehyde addition products. However, the cost associated with producing fibers crosslinked with dialdehyde crosslinking agents such as glutaraldehyde may be too high to result in significant commercial success. Therefore, there is a need to find cellulosic fiber crosslinking agents which are both safe for use on the human skin, good aesthetics (exhibit low odor, have high fiber brightness), and also are commercially feasible.

The use of specific polycarboxylic acids to crosslink cellulosic fibers is also known in the art. See, for example, U.S. Pat. No. 5,137,537, Herron et al., issued Aug. 11, 1992, U.S. Pat. No. 5,183,707, Herron et al., issued Feb. 2, 1993, and U.S. Pat. No. 5,190,563, Herron et al., issued Mar. 2, 1993. The Herron et al. references disclose absorbent structures containing individualized cellulosic fibers crosslinked with a $C_2$–$C_9$ polycarboxylic acid. The ester crosslink bonds formed by the polycarboxylic acid crosslinking agents are different from the crosslink bonds that result from the mono- and di-aldehyde crosslinking agents, which form acetal crosslinked bonds.

Absorbent structures made from these individualized, ester-crosslinked fibers exhibit increased wet resilience and dry resilience and improved responsiveness to wetting relative to structures containing uncrosslinked fibers. Furthermore, the preferred polycarboxylic crosslinking agent i.e., citric acid, is available in large quantities at relatively low prices making it commercially competitive with formaldehyde and formaldehyde addition products. Unfortunately, the preferred $C_2$–$C_9$ crosslinking agent, citric acid, can cause discoloring (i.e., yellowing) of the white cellulosic fibers when treated at elevated temperatures. In addition, unpleasant odors can also be associated with the use of alpha-hydroxy carboxylic acids such as citric acid. The Herron et al. references do not include processes by which to reduce the odor or increase fiber brightness.

It has now been discovered that the characteristic odor can be removed and the brightness improved by contacting the fibers with an alkaline solution (e.g., an aqueous solution of sodium hydroxide) and an oxidizing bleaching agent (e.g., hydrogen peroxide). The alkaline solution raises the finished fiber pH preferably to the 5.5–6.5 range from about 4.5. This in combination with the oxidizing bleaching agent eliminates the "smokey and burnt" odor characteristics of the crosslinked fibers. The oxidizing bleaching agent when added at high consistency increases the final product brightness to 80 to 86 from 70 to 75, and reduces odor.

It is an object of this invention to provide a process for preparing reduced odor and brighter individualized fibers crosslinked with a polycarboxylic acid crosslinking agent which have improved absorbency and aesthetic properties. Absorbent structures made from the individualized, polycarboxylic acid crosslinked fibers exhibit higher wet resilience and higher dry resilience than structures made from uncrosslinked fibers.

It is a further an object of this invention to provide individualized fibers crosslinked with a polycarboxylic crosslinking agent and contacted with an alkaline solution and oxidizing agent and absorbent structures made from such fibers as described above, which have a superior balance of aesthetic properties relative to prior known crosslinked fibers.

It is a further object of this invention to provide reduced odor and improved brightness individualized fibers crosslinked with a polycarboxylic crosslinking agent and absorbent structures made from such fibers, as described above, which have a superior balance of absorbency properties relative to prior known crosslinked fibers.

It is additionally an object of this invention to provide a commercially viable process for preparing reduced odor and brighter individualized, crosslinked fibers and absorbent structures made from such fibers, as described above, which can be safely utilized in the vicinity of human skin.

SUMMARY OF THE INVENTION

It has been found that improved absorbent structure performance for structures containing reduced odor and brighter individualized, crosslinked fibers may be obtained through the utilization of individualized, crosslinked fibers made according to the process disclosed herein.

Accordingly, such fibers are prepared by practicing the following process, which includes the steps of:
  a. providing cellulosic fibers;
  b. contacting the fibers with a solution containing a crosslinking agent selected from the group consisting of $C_2$–$C_9$ polycarboxylic acids;
  c. mechanically separating the fibers into substantially individual form;
  d. drying the fibers and reacting the crosslinking agent with the fibers to form crosslink bonds while the fibers are in substantially individual form, to form intrafiber crosslink bonds; and
  e. raising the pH of the crosslinked fibers to at least about 5, by contacting said crosslinked fibers with an alkaline solution.

The individualized cellulosic fibers are contacted with a sufficient amount of crosslinking agent such that an effective amount, preferably between about 0.1 weight % and about 10.0 weight %, more preferably between about 3.0 weight % and about 8.0 weight % crosslinking agent, calculated on a dry fiber weight basis, reacts with the fibers to form intrafiber crosslink bonds. The crosslinked individualized cellulosic fibers are contacted with a sufficient amount of an alkaline solution, preferably from about 0.07 weight % to about 1.8 weight % of the alkaline compound, to raise the pH of the fibers to at least about 5, preferably from about 5 to about 7, and most preferably, from about 5.5 to about 6.5. For some applications, the pH can go as high as 10.5. The fibers are also contacted with a strong oxidizing bleaching agent, preferably from about 0.02 weight % to about 1.5 weight %. It has been found that the combination of treating the fibers with an alkaline solution and a oxidizing agent effectively reduces the odor of the fibers and increases their final brightness.

Without being bound by theory, it is believed that raising the final fiber pH from about 4.5 to about 10.5 preferably from about 5.5 to about 6.5 by use of an alkaline solution changes the phenolics to the phenolate form which are not volatile. Phenolates are not easily vaporized at the higher pH. In addition, higher pH would preclude the possibility of forming significant amounts of hydrogen sulfide. Secondly, it is believed that the alkaline oxidizing agent (e.g., hydrogen peroxide) oxidizes the sugar decomposition markers such as furfural, methyl furfural and guaicols and reduces the amount of citric acid anhydrides.

The amount of alkaline solution and oxidizing agent preferably utilized is of course dependent upon the particular agents used and the reaction conditions, especially temperature and airflow. In a preferred embodiment, the fibers are contacted after curing and during re-moisturization with sodium hydroxide (18% technical grade) being added at a ratio of approximately 10 pounds to 20 pounds per ton of bone dry fiber. Hydrogen peroxide (19% technical grade) is added at approximately 4 pounds to 20 pounds per ton of bone dry fiber. The sodium hydroxide is added at the suction of the re-moisturization pump and the hydrogen peroxide is added just before the re-moisturization spray nozzle as the mixture enters the fiber stream. This results in a crosslinked fiber that contains 10% moisture and a final pH of 5.5 to 6.5 based on the amount of chemicals employed.

The above described process steps of raising the pH of the crosslinked fibers and contacting the crosslinked fibers with an oxidizing agent are preferably carried out concurrently to simplify the process of the present invention. However, the two process steps can also be carried out sequentially. For example, the fibers could be first contacted with an alkaline solution to raise the fibers' pH, and then contacted with the oxidizing agent. Alternatively, the crosslinked fibers could first be contacted with an oxidizing agent, and then contacted with the alkaline solution. Thus, the present invention should not be construed as requiring the addition of the alkaline solution and the oxidizing agent to the crosslinked fibers to be carried out in any particular order.

Preferably the fibers are crosslinked while in a highly twisted condition. In the most preferred embodiments, the fibers are contacted with crosslinking agent in an aqueous solution, dewatered, mechanically separated into substantially individual form, and then dried and caused to crosslink under substantially unrestrained conditions. The dewatering, mechanical separation, and drying stages allow the fibers to become highly twisted prior to crosslinking. The twisted condition is then at least partially but less than completely set as a result of crosslinking. Preferably, the fibers are contacted with the alkaline solution and the oxidizing agent after crosslinking has been completed.

DETAILED DESCRIPTION OF THE INVENTION

Cellulosic fibers of diverse natural origin are applicable to the invention. Digested fibers from softwood, hardwood or cotton linters are preferably utilized. Fibers from Esparto grass, bagasse, kemp, flax, and other ligneous and cellulosic fiber sources may also be utilized as raw material in the invention. The fibers may be supplied in slurry, unsheeted or sheeted form. Fibers supplied as wet lap, dry lap or other sheeted form are preferably rendered into unsheeted form by mechanically disintegrating the sheet, preferably prior to contacting the fibers with the crosslinking agent. Also, preferably the fibers are provided in a wet or moistened condition. Most preferably, the fibers are never-dried fibers. In the case of dry lap, it is advantageous to moisten the fibers prior to mechanical disintegration in order to minimize damage to the fibers.

The optimum fiber source utilized in conjunction with this invention will depend upon the particular end use contemplated. Generally, pulp fibers made by chemical pulping processes are preferred. Completely bleached, partially bleached and unbleached fibers are applicable. It may frequently be desired to utilize bleached pulp for its superior brightness and consumer appeal. Wood fibers that have been at least partially bleached are preferred for use in the process of the present invention. For products such as paper towels and absorbent pads for diapers, sanitary napkins, catamenials, and other similar absorbent paper products, it is especially preferred to utilize fibers from southern softwood pulp due to their premium absorbency characteristics.

Crosslinking agents applicable to the present development include aliphatic and alicyclic $C_2$–$C_9$ polycarboxylic acids. As used herein, the term "$C_2$–$C_9$ polycarboxylic acid" refers to an organic acid containing two or more carboxyl (COOH) groups and from 2 to 9 carbon atoms in the chain or ring to which the carboxyl groups are attached. The carboxyl groups are not included when determining the number of carbon atoms in the chain or ring. For example, 1,2,3 propane tricarboxylic acid would be considered to be a $C_3$ polycarboxylic acid containing three carboxyl groups. Similarly, 1,2,3,4 butane tetracarboxylic acid would be considered to be a $C_4$ polycarboxylic acid containing four carboxyl groups.

More specifically, the $C_2$–$C_9$ polycarboxylic acids suitable for use as cellulose crosslinking agents in the present invention include aliphatic and alicyclic acids either olefinically saturated or unsaturated with at least three and preferably more carboxyl groups per molecule or with two carboxyl groups per molecule if a carbon—carbon double bond is present alpha, beta to one or both carboxyl groups. An additional requirement is that to be reactive in esterifying cellulose hydroxyl groups, a given carboxyl group in an aliphatic or alicyclic polycarboxylic acid must be separated from a second carboxyl group by no less than 2 carbon atoms and no more than three carbon atoms. Without being bound by theory, it appears from these requirements that for a carboxyl group to be reactive, it must be able to form a cyclic 5- or 6-membered anhydride ring with a neighboring carboxyl group in the polycarboxylic acid molecule. Where two carboxyl groups are separated by a carbon—carbon double bond or are both connected to the same ring, the two carboxyl groups must be in the cis configuration relative to each other if they are to interact in this manner.

In aliphatic polycarboxylic acids containing three or more carboxyl groups per molecule, a hydroxyl group attached to a carbon atom alpha to a carboxyl group does not interfere with the esterification and crosslinking of the cellulosic fibers by the acid. Thus, polycarboxylic acids such as citric acid (also known as 2-hydroxy-1,2,3 propane tricarboxylic acid) and tartrate monosuccinic acids are suitable as crosslinking agents in the present development.

The aliphatic or alicyclic $C_2$–$C_9$ polycarboxylic acid crosslinking agents may also contain an oxygen or sulfur atom(s) in the chain or ring to which the carboxyl groups are attached. Thus, polycarboxylic acids such as oxydisuccinic acid also known as 2,2'-oxybis(butanedioic acid), thiodisuccinic acid, and the like, are meant to be included within the scope of the invention. For purposes of the present invention, oxydisuccinic acid would be considered to be a $C_2$–$C_9$ polycarboxylic acid containing four carboxyl groups.

Examples of specific polycarboxylic acids which fall within the scope of this invention include the following: maleic acid, citraconic acid also known as methylmaleic acid, citric acid, itaconic acid also known as methylenesuccinic acid, tricarballylic acid also known as 1,2,3 propane tricarboxylic acid, trans-aconitic acid also known as trans-1-propene-1,2,3-tricarboxylic acid, 1,2,3,4-butanetetracarboxylic acid, all-cis-1,2,3,4-cyclopentanetetracarboxylic acid, mellitic acid also known as benzenehexacarboxylic acid, and oxydisuccinic acid also known as 2,2'-oxybis(butanedioic acid). The above list of specific polycarboxylic acids is for exemplary purposes only, and is not intended to be all inclusive. Importantly, the crosslinking agent must be capable of reacting with at least two hydroxyl groups on proximately located cellulose chains in a single cellulosic fiber.

Preferably, the $C_2$–$C_9$ polycarboxylic acids used herein are aliphatic, saturated, and contain at least three carboxyl groups per molecule. One group of preferred polycarboxylic acid crosslinking agents for use with the present invention includes citric acid also known as 2-hydroxy-1,2,3 propane tricarboxylic acid, 1,2,3 propane tricarboxylic acid, and 1,2,3,4 butane tetracarboxylic acid. Citric acid is especially preferred, since it has provided fibers with high levels of absorbency and resiliency, is safe and non-irritating to human skin, an has provided stable, crosslink bonds. Furthermore, citric acid is available in large quantities at relatively low prices, thereby making it commercially feasible for use as a crosslinking agent.

Another group of preferred crosslinking agents for use in the present invention includes saturated $C_2$–$C_9$ polycarboxylic acids containing at least one oxygen atom in the chain to which the carboxyl groups are attached. Examples of such compounds include oxydisuccinic acid, tartrate monosuccinic acid having the structural formula:

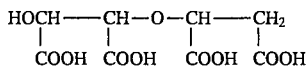

and tartrate disuccinic acid having the structural formula:

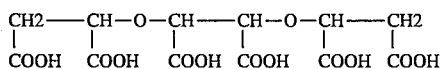

A more detailed description of tartrate monosuccinic acid, tartrate disuccinic acid, and salts thereof, can be found in U.S. Pat. No. 4,663,071, Bush et al., issued May 5, 1987, incorporated herein by reference.

Those knowledgeable in the area of polycarboxylic acids will recognize that the aliphatic and alicyclic $C_2$–$C_9$ polycarboxylic acid crosslinking agents described above may be present in a variety of forms, such as the free acid form, and salts thereof. Although the free acid form is preferred, all such forms are meant to be included within the scope of the invention.

The individualized, crosslinked fibers of the present invention have an effective amount of the $C_2$–$C_9$ polycarboxylic acid crosslinking agent reacted with the fibers in the form of intrafiber crosslink bonds. As used herein, "effective amount of crosslinking agent" refers to an amount of crosslinking agent sufficient to provide an improvement in at least one significant absorbency property of the fibers themselves and/or absorbent structures containing the individualized, crosslinked fibers, relative to conventional, uncrosslinked fibers. One example of a significant absorbency property is drip capacity, which is a combined measured of an absorbent structure's fluid absorbent capacity and fluid absorbency rate. A detailed description of the procedure for determining drip capacity is provided hereinafter.

In particular, unexpectedly good results are obtained for absorbent pads made from individualized, crosslinked fibers having between about 1.0 weight % and about 10.0 weight %, more preferably between about 3.0 weight % and about 8.0 weight % crosslinking agent, calculated on a dry fiber weight basis, reacted with the fibers. Preferably, the fibers are contacted with from about 0.07% to about 1.8 weight % of an alkaline compound and from about 0.02% to about 1.5 weight % strong oxidizing agent after the crosslinking reaction has taken place.

Preferably, the crosslinking agent is contacted with the fibers under such conditions that the crosslinking agent penetrates into the interior of the individual fiber structures. This includes spraying of the fibers of a pulp sheet.

Applicants have discovered that the crosslinking reaction can be accomplished at practical rates without a catalyst, provided the pH is kept within a particular range (to be discussed in more detail below). This is contrary to the prior art which teaches that specific catalysts are needed to provide sufficiently rapid esterification and crosslinking of fibrous cellulose by polycarboxylic acid crosslinking agents to be commercially feasible. See, for example, U.S. Pat. No. 4,820,307, Welch et al., issued Apr. 11, 1989.

However, if desired, the fibers can also be contacted with an appropriate catalyst prior to crosslinking. Applicants have found that the type, amount, and method of contact of catalyst to the fibers will be dependent upon the particular crosslinking process practiced. These variables will be discussed in more detail below.

Once the fibers are treated with crosslinking agent (and catalyst if one is used), the crosslinking agent is caused to react with the fibers in the substantial absence of interfiber bonds, i.e., while interfiber contact is maintained at a low degree of occurrence relative to unfluffed pulp fibers, or the fibers are submerged in a solution that does not facilitate the formation of interfiber bonding, especially hydrogen bonding. This results in the formation of crosslink bonds which are intrafiber in nature. Under these conditions, the crosslinking agent reacts to form crosslink bonds between hydroxyl groups of a single cellulose chain or between hydroxyl groups of approximately located cellulose chains of a single cellulosic fiber.

Although not presented or intended to limit the scope of the invention, it is believed that the carboxyl groups on the polycarboxylic acid crosslinking agent react with the hydroxyl groups of the cellulose to form ester bonds. The formation of ester bonds, believed to be the desirable bond type providing stable crosslink bonds, is favored under acidic reaction conditions. Therefore, acidic crosslinking conditions, i.e. pH ranges of from about 1.5 to about 5, are highly preferred for the purposes of this invention.

The fibers are preferably mechanically defibrated into a low density, individualized, fibrous form known as "fluff" prior to reaction of the crosslinking agent with the fibers. Mechanical defibration may be performed by a variety of methods which are presently known in the art or which may hereafter become known. Mechanical defibration is preferably performed by a method wherein knot formation and fiber damage are minimized. One type of device which has been found to be particularly useful for defibrating the cellulosic fibers is the three stage fluffing device described in U.S. Pat. No. 3,987,968, issued to D. R. Moore and O. A. Shields on Oct. 26, 1976, said patent being hereby expressly incorporated by reference into this disclosure. The fluffing device described in U.S. Pat. No. 3,987,968 subjects moist cellulosic pulp fibers to a combination of mechanical impact, mechanical agitation, air agitation and a limited amount of air drying to create a substantially knot-free fluff. The individualized fibers have imparted thereto an enhanced degree of curl and twist relative to the amount of curl and twist naturally present in such fibers. It is believed that this additional curl and twist enhances the resilient character of absorbent structures made from the finished, crosslinked fibers.

Other applicable methods for defibrating the cellulosic fibers include, but are not limited to, treatment with a Waring blender and tangentially contacting the fibers with a rotating disk refiner or wire brush. Preferably, an air stream is directed toward the fibers during such defibration to aid in separating the fibers into substantially individual form.

Regardless of the particular mechanical device used to form the fluff, the fibers are preferably mechanically treated while initially containing at least about 20% moisture, and preferably containing between about 40% and about 65% moisture.

Mechanical refining of fibers at high consistency or of partially dried fibers may also be utilized to provide curl or twist to the fibers in addition to curl or twist imparted as a result of mechanical defibration.

The fibers made according to the present invention have unique combinations of stiffness and resiliency, low odor and high brightness, which allow absorbent structures made from the fibers to maintain high levels of absorptivity, and exhibit high levels of resiliency and an expansionary responsiveness to wetting of a dry, compressed absorbent structure. In addition to having the levels of crosslinking within the stated ranges, the crosslinked fibers are characterized by having water retention values (WRV's) of less than about 60, more preferably between about 28 to about 50, and most preferably between about 30 and about 45, for conventional, chemically pulped, papermaking fibers and odor levels of "smokey" and "burnt" of less than two, preferably between 0 and about 1. The characteristics of the headspace contain reduced levels of sugar decomposition markers and anhydrides. In addition, the final pH is preferably between about 5.5 and about 6.5 and the brightness is above 80. The WRV of a particular fiber is indicative of the level of crosslinking. Very highly crosslinked fibers, such as those produced by many of the prior art known crosslinking processes previously discussed, have been found to have WRV's of less than about 25, and generally less than about 20. The particular crosslinking process utilized will, of course, affect the WRV of the crosslinked fiber. However, any process which will result in crosslinking levels and WRV's within the stated limits is believed to be, and is intended to be, within the scope of this invention. Applicable methods of crosslinking include dry crosslinking processes and nonaqueous solution crosslinking processes as generally discussed in the Background Of The Invention. Certain preferred dry crosslinking and nonaqueous solution crosslinking processes for preparing the individualized, crosslinked fibers of the present invention, will be discussed in more detail below. Aqueous solution crosslinking processes wherein the solution causes the fibers to become highly swollen will result in fibers having WRV's which are in excess of about 60. These fibers will provide insufficient stiffness and resiliency for the purposes of the present invention.

Specifically referring to dry crosslinking processes, reduced odor individualized, crosslinked fibers may be produced from such a process by providing a quantity of cellulosic fibers, contacting a pulp sheet of fibers with a type and amount of crosslinking agent as described above, mechanically separating, e.g., defibrating, the fibers into substantially individual form, drying the fibers and causing the crosslinking agent to react with the fibers in the presence of a catalyst to form crosslink bonds while the fibers are maintained in substantially individual form and contacting the crosslinked fibers with an alkaline solution and oxidizing agent to reduce the odor and brighten the fibers. The defibration step, apart from the drying step, is believed to impart additional curl. Subsequent drying is accompanied by twisting of the fibers, with the degree of twist being enhanced by the curled geometry of the fiber. As used herein, fiber "curl" refers to a geometric curvature of the fiber about the longitudinal axis of the fiber. "Twist" refers to a rotation of the fiber about the perpendicular cross-section of the longitudinal axis of the fiber. The fibers of the preferred embodiment of the present invention are individualized, crosslinked in intrafiber bond form, and are highly twisted and curled.

As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The distance between nodes corresponds to an axial rotation of 180°. Those skilled in the art will recognize that the occurrence of a twist node as described above, is primarily a visual rather than a physical phenomena. However, the number of twist nodes in a certain length of fibers (i.e., the twist count) is directly indicative of the degree of fiber twist, which is a physical parameter of the fiber. The appearance and quantity of twist nodes will vary depending upon whether the fiber is a summerwood fiber or a springwood fiber. The twist nodes and total twist count are determined by a Twist Count Image Analysis Method which is described in the Experimental Method section of the disclosure. The average twist count referred to in describing the fibers of the present invention is properly determined by the aforementioned twist count method. When counting twist nodes, portions of fiber darkened due to fiber damage or fiber compression should be distinguished from portions of fiber appearing darkened due to fiber twisting.

The actual twist count of any given sample of fibers will vary depending upon the ratio of springwood fibers to summerwood fibers. The twist count of any particular springwood or summerwood fibers will also vary from fiber to fiber. Notwithstanding the above, the average twist count limitations are useful in defining the present invention, and these limitations apply regardless of the particular combination of springwood fibers and summerwood fibers. That is, any mass of fibers having twist count encompassed by the stated twist count limitations are meant to be encompassed within the scope of the present invention, so long as the other claimed limitations are met.

In the measurement of twist count for a sample of fibers, it is important that a sufficient amount of fibers be examined in order to accurately represent the average level of twist of the variable individual fiber twist levels. It is suggested that at least five (5) inches of cumulative fiber length of a representative sample of a mass of fibers be tested in order to provide a representative fiber twist count.

The wet fiber twist count is described and measured analogously to the dry fiber twist count, said method varying only in that the fiber is wetted with water prior to being treated and the twist nodes are then counted while wet in accordance with the Twist Count Image Analysis Method.

Preferably, the average dry fiber twist count is at least about 2.5 twist nodes per millimeter, and the average wet fiber twist count is at least about 1.5 twist nodes per millimeter and is at least 1.0 twist nodes per millimeter less than its dry fiber twist count. Most preferably, the average dry fiber twist count is at least about 3.0 twist nodes per millimeter, and the average wet fiber twist count is at least about 2.0 twist nodes per millimeter and is at least 1.0 twist nodes per millimeter less than the dry fiber twist count.

In addition to being twisted, the fibers of the present invention are curled. Fiber curl may be described as a fractional shortening of the fiber due to kinks, twists, and/or bends in the fiber. For the purposes of this disclosure, fiber curl shall be measured in terms of a two dimensional field. The level of fiber curl shall be referred to in terms of a fiber curl index. The fiber curl factor, a two dimensional measurement of curl, is determined by viewing the fiber in a two dimensional plane, measuring the projected length of the fiber as the longest dimension of a rectangle encompassing the fiber, $L_R$, and the actual length of the fiber $L_A$, and then calculating the fiber curl factor from the following equation:

$$\text{Curl Factor} = (L_A/L_R) - 1 \quad (1)$$

A Fiber Curl Index Image Analysis Method is utilized to measure $L_R$ and $L_A$. This method is described in the Experimental Methods section of this disclosure. The background information for this method is described in the 1979 International Paper Physics Conference Symposium, The Harrison Hotel, Harrison Hot Springs, British Columbia, Sep. 17–19, 1979 in a paper titled "Application Of Image Analysis To Pulp Fiber Characterization: Part 1," by B. D. Jordan and D. H. Page, pp. 104–114, Canadian Pulp and Paper Association (Montreal, Quebec, Canada), said reference being incorporated by reference into this disclosure.

Preferably, the fibers have a curl factor of at least about 0.30, and more preferably of at least about 0.50.

Maintaining the fibers in substantially individual form during drying and crosslinking allows the fibers to twist during drying and thereby be crosslinked in such twisted, curled state. Drying fibers under such conditions that the fibers may twist and curl is referred to as drying the fibers under substantially unrestrained conditions. On the other hand, drying fibers in sheeted form results in dried fibers which are not as highly twisted and curled as fibers dried in substantially individualized form. It is believed that interfiber hydrogen bonding "restrains" the relative occurrence of twisting and curling of the fiber.

There are various methods by which the fibers may be contacted with the crosslinking agent and catalyst (if a catalyst is used). In one embodiment, the fibers in pulp sheet form are contacted with a solution which initially contains both the crosslinking agent and the catalyst. In another embodiment, the fibers are contacted with an aqueous solution of crosslinking agent and allowed to soak prior to addition of the catalyst. The catalyst is subsequently added. In a third embodiment, the crosslinking agent and catalyst are added to an aqueous slurry of the cellulosic fibers. Other methods in addition to those described herein will be apparent to those skilled in the art, and are intended to be included within the scope of this invention. Regardless of the particular method by which the fibers are contacted with crosslinking agent and catalyst (if a catalyst is used), the cellulosic fibers, crosslinking agent and catalyst are preferably mixed and/or allowed to soak sufficiently with the fibers to assure thorough contact with and impregnation of the individual fibers.

There are various methods by which the crosslinked fibers may be contacted with the odor reducing and brightening agent. In one embodiment, the fibers are contacted after being discharged from the drying stage in an air stream. The fibers are initially dry and after chemicals and fibers have been contacted the consistency is approximately 90%. The final pH is between 5.5 and 6.5.

Applicants have discovered that the crosslinking reaction can be accomplished without the use of a catalyst if the pH of the solution containing the crosslinking agent is kept within the ranges specified hereinafter. In particular, the aqueous portion of the cellulosic fiber slurry or crosslinking agent solution should be adjusted to a target pH of between about pH 1.5 and about pH 5, more preferably between about pH 2.0 and about pH 3.5, during the period of contact between the crosslinking agent and the fibers. Preferably, the pH is adjusted by the addition of a base, such as sodium hydroxide, to the crosslinking agent solution.

Notwithstanding the above, in general, any substance which can catalyze the crosslinking mechanism may be utilized. Applicable catalysts include alkali metal hypophosphites, alkali metal phosphites, alkali metal polyphosphates, alkali metal phosphates, and alkali metal sulfates. Especially preferred catalysts are the alkali metal hypophosphites, alkali metal phosphates, and alkali metal sulfates. The mechanism of the catalysis is unknown, although applicants believe that the catalysts may simply be functioning as buffering agents, keeping the pH levels within the desired ranges. A more complete list of catalysts useful herein can be found in U.S. Pat. No. 4,820,307, Welch et al, issued Apr. 11, 1989, incorporated herein by reference. The selected catalyst may be utilized as the sole catalyzing agent, or in combination with one or more other catalysts.

The amount of catalyst preferably utilized is, of course, dependent upon the particular type and amount of crosslinking agent and the reaction conditions, especially temperature and pH. In general, based upon technical and economic considerations, catalyst levels of between about 5 wt. % and about 80 wt. %, based on the weight of crosslinking agent added to the cellulosic fibers, are preferred. For exemplary purposes, in the case wherein the catalyst utilized is sodium hypophosphite and the crosslinking agent is citric acid, a catalyst level of about 50 wt. %, based upon the amount of citric acid added, is preferred. It is additionally desirable to adjust the aqueous portion of the cellulosic fiber slurry or crosslinking agent solution to a target pH of between about pH 1.5 and about pH 5, more preferably between about pH 2.0 and about pH 3.5, during the period of contact between the crosslinking agent and the fibers. The amount of alkaline solution and oxidizing agent preferably utilized is of course, dependent upon the particular agents used and the reaction conditions, especially temperature, time and air flow. In general, based upon technical and economic considerations, alkaline compound levels between 0.07 to 1.8 weight % and oxidizing agent levels between 0.02 to 1.5 weight % are preferred. The final pH is preferably between about 5.5 and about 6.5.

The cellulosic fibers should generally be dewatered and optionally dried. The workable and optimal consistencies will vary depending upon the type of fluffing equipment utilized. In the preferred embodiments, the cellulosic fibers are dewatered and optimally dried to a consistency of between about 20% and about 80%. More preferably, the fibers are dewatered and dried to a consistency level of between about 35% and about 60%. Drying the fibers to within these preferred ranges generally will facilitate defibration of the fibers into individualized form without excessive formation of knots associated with higher moisture levels and without high levels of fiber damage associated with lower moisture levels.

For exemplary purposes, dewatering may be accomplished by such methods as mechanically pressing, centrifuging, or air drying the pulp. Additional drying of the fibers within the 35–60% consistency range previously described is optional but is preferably performed by a method, known in the art as air drying, under conditions such that the utilization of high temperature for an extended period of time is not required. Excessively high temperature and time in this stage may result in drying the fibers beyond 60% consistency, thereby possibly producing excessive fiber damage during the ensuing defibration stage. After dewatering, the fibers are then mechanically defibrated as previously described.

The defibrated fibers are then dried to between 60% and 100% consistency by a method known in the art as flash drying. This stage imparts additional twist and curl to the fibers as water is removed from them. While the amount of water removed by this additional drying step may be varied, it is believed that flash drying to higher consistency provides a greater level of fiber twist and curl than does flash drying to a consistency in the lower part of the 60%–100% range. In the preferred embodiments, the fibers are dried to about 90%–95% consistency. It is believed that this level of flash drying provides the desired level of fiber twist and curl without requiring the higher flash drying temperatures and retention times required to reach 100% consistency. Flash drying the fibers to a consistency, such as 90%–95%, in the higher portion of the 60%–100% range also reduces the amount of drying which must be accomplished in the curing stage following flash drying.

The flash dried fibers are then heated to a suitable temperature for an effective period of time to cause the crosslinking agent to cure, i.e., to react with the cellulosic fibers. The rate and degree of crosslinking depends upon dryness of the fiber, temperature, pH, amount and type of catalyst and crosslinking agent and the method utilized for heating and/or drying the fibers while crosslinking is performed. Crosslinking at a particular temperature will occur at a higher rate for fibers of a certain initial moisture content when accompanied by a continuous, air-through drying than when subjected to drying/heating in a static oven. Those skilled in the art will recognize that a number of temperature-time relationships exist for the curing of the crosslinking agent. Drying temperatures from about 145° C. to about 165° C. for periods of between about 30 minutes and 60 minutes, under static, atmospheric conditions will generally provide acceptable curing efficiencies for fibers having moisture contents less than about 10%. Those skilled in the art will also appreciate that higher temperatures and forced air convection decrease the time required for curing. Thus, drying temperatures from about 170° C. to about 190° C. for periods of between about 2 minutes and 20 minutes, in an air-through oven will also generally provide acceptable curing efficiencies for fibers having moisture contents less than about 10%. Curing temperatures should be maintained at less than about 225° C., preferably less than about 200° C., since exposure of the fibers to such high temperatures may lead to darkening or other damaging of the fibers.

Without being bound by theory, it is believed that the chemical reaction of the cellulosic fibers with the $C_2$–$C_9$ polycarboxylic acid crosslinking agent does not begin until the mixture of these materials is heated in the curing oven. During the cure stage, ester crosslink bonds are formed between the $C_2$–$C_9$ polycarboxylic acid crosslinking agent and the cellulose molecules. These ester cross linkages are mobile under the influence of heat, due to a transesterification reaction which takes place between ester groups and adjacent unesterified hydroxyl groups on the cellulosic fibers. It is further believed that the process of transesterification, which occurs after the initial ester bonds are formed, results in fibers which have improved absorbency properties compared to fibers that are not cured sufficiently to allow transesterification to occur.

Following the crosslinking step, the fibers are post treated to reduce the odor and to increase the brightness. The fibers are contacted with an alkaline solution and oxidizing agent. The alkaline solution comprises an aqueous medium and an alkaline compound. The alkaline compound is preferably selected from the group consisting of sodium hydroxide, sodium hypochlorite, sodium bisulfite, ammonium hydroxide, and mixtures thereof, with sodium hydroxide being most preferred. The pH of the alkaline solution is preferably greater than about 9.

The oxidizing bleaching agent is preferably selected from the group consisting of hydrogen peroxide, sodium peroxide, peracetic acid, chlorine dioxide, sodium hypochlorite, hydrogen chloride, and mixtures thereof, with hydrogen peroxide being most preferred. Although, other chemicals that function as bleaching agents may also be used.

The pH of the fibers is preferably raised and maintained at a level of from about 5.5 to about 6.5. It is important that these agents not be introduced prior to the fibers being crosslinked, and preferably that the final pH remain below 7.0. Single treatments of the fibers by spraying sodium hydroxide and hydrogen peroxide onto an air stream containing the fibers was observed to reduce the odor to zero and increase the brightness to 80–86 from approximately 75. The fibers when first contacted with these agents are preferably initially bone dry and preferably, remain below 10% total moisture. This method is believed to embody the preferred manner of producing reduced odor crosslinked fibers, since the capital expense and processing inconvenience of additional bleaching and washing are avoided. In addition, conventional multi-stage bleaching and washing stages following crosslinking, have been found to provide desirable results. These would include DEP or DEH stages where D is chlorine dioxide, E is caustic extraction, P is peroxide and H is sodium hypochlorite. The post-crosslinking sequence stages are preferably alkaline treatments, but the final pH should be adjusted to be below 7.

The maximum level of crosslinking will be achieved when the fibers are essentially dry (having less than about 5% moisture). Due to this absence of water, the fibers are crosslinked while in a substantially unswollen, collapsed state. Consequently, they characteristically have low fluid retention values (FRV) relative to the range applicable to this invention. The FRV refers to the amount of fluid calculated on a dry fiber basis, that remains absorbed by a sample of fibers that have been soaked and then centrifuged to remove interfiber fluid. (The FRV is further defined and the Procedure For Determining FRV, is described below.) The amount of fluid that the crosslinked fibers can absorb is dependent upon their ability to swell upon saturation or, in other words, upon their interior diameter or volume upon swelling to a maximum level. This, in turn, is dependent upon the level of crosslinking. As the level of intrafiber crosslinking increases for a given fiber and process, the FRV of the fiber will decrease. Thus, the FRV value of a fiber is structurally descriptive of the physical condition of the fiber at saturation. Unless otherwise expressly indicated, FRV data described herein shall be reported in terms of the water retention value (WRV) of the fibers. Other fluids, such as salt water and synthetic urine, may also be advantageously utilized as a fluid medium for analysis. Generally, the FRV of a particular fiber crosslinked by procedures wherein curing is largely dependent upon drying, such as the present process, will be primarily dependent upon the crosslinking agent and the level of crosslinking. The WRV's of fibers crosslinked by this dry crosslinking process at crosslinking agent levels applicable to this invention are generally less than about 60, greater than about 28, preferably less than about 50, and more preferably between about 30 and about 45. Bleached southern softwood kraft (SSK) fibers having between about 1.0 weight % and about 10.0 weight % citric acid reacted thereon, calculated on a dry fiber weight basis, have been observed to have WRV's respectively ranging from about 28 to about 40. The degree of bleaching and the practice of post-crosslinking bleaching steps have been found to affect WRV. SSK fibers prepared by many of the prior art known crosslinking processes have levels of crosslinking higher than described herein, and have WRV's less than about 25. Such fibers, as previously discussed, have been observed to be exceedingly stiff and to exhibit lower absorbent capabilities than the fibers of the present invention.

In another process for making individualized, crosslinked fibers by a dry crosslinking process, cellulosic fibers are contacted with a solution containing a crosslinking agent as described above. Either before or after being contacted with the crosslinking agent, the fibers are provided in a sheet form. The fibers, while in sheeted form, are dried and caused to crosslink preferably by heating the fibers to a temperature of between about 120° C. and about 160° C. Subsequent to crosslinking, the fibers are mechanically separated into substantially individual form. This is preferably performed by treatment with a fiber fluffing apparatus such as the one described in U.S. Pat. No. 3,987,968 or may be performed with other methods for defibrating fibers as may be known in the art. The individualized, crosslinked fibers made according to this sheet crosslinking process are treated with a sufficient amount of crosslinking agent such that an effective amount of crosslinking agent, preferably between about 1.0 weight % and about 10.0 weight % crosslinking agent, calculated on a cellulose anhydroglucose molar basis and measured subsequent to defibration, are reacted with the fibers in the form of intrafiber crosslink bonds. Another effect of drying and crosslinking the fibers while in sheet form is that fiber to fiber bonding restrains the fibers from twisting and curling with increased drying. Compared to individualized, crosslinked fibers made according to a process wherein the fibers are dried under substantially unrestrained conditions and subsequently crosslinked in a twisted, curled configuration, absorbent structures containing the relatively untwisted fibers made by the sheet curing process described above would be expected to exhibit lower wet resiliency and lower responsiveness to wetting.

It is also contemplated to mechanically separate the fibers into substantially individual form between the drying and the crosslinking step. That is, the fibers are contacted with the crosslinking agent and subsequently dried while in sheet form. Prior to crosslinking, the fibers are individualized to facilitate intrafiber crosslinking. This alternative crosslinking method, as well as other variations which will be apparent to those skilled in the art, are intended to be within the scope of this invention.

Another category of crosslinking processes applicable to the present invention is nonaqueous solution cure crosslinking processes. The same types of fibers applicable to dry crosslinking processes may be used in the production of nonaqueous solution crosslinked fibers. The fibers are treated with a sufficient amount of crosslinking agent such that an effective amount of crosslinking agent subsequently reacts with the fibers, and with an appropriate catalyst, if desired. The amounts of crosslinking agent and catalyst (if one is used) utilized will depend upon such reaction conditions as consistency, temperature, water content in the crosslinking solution and fibers, type of crosslinking agent and diluent in the crosslinking solution, and the amount of crosslinking desired. The crosslinking agent is caused to react while the fibers are submerged in a substantially nonaqueous crosslinking solution. The nonaqueous crosslinking solution contains a nonaqueous, water-miscible, polar diluent such as, but not limited to, acetic acid, propanoic acid, or acetone. The crosslinking solution may also contain a limited amount of water or other fiber swelling liquid, however, the amount of water is preferably insufficient to induce any substantial levels of fiber swelling. Crosslinking solution systems applicable for use as a crosslinking medium include those disclosed in U.S. Pat. No. 4,035,147, issued to S. Sangenis, G. Guiroy, and J. Quere, on Jul. 12, 1977, which is hereby incorporated by reference into this disclosure.

The crosslinked fibers of the present invention are preferably prepared in accordance with the previously described dry crosslinking process. The crosslinked fibers of the present invention may be utilized directly in the manufacture of air laid absorbent cores. Additionally, due to their stiffened and resilient character, the crosslinked fibers may be wet laid into an uncompacted, low density sheet which, when subsequently dried, is directly useful without further mechanical processing as an absorbent core. The crosslinked fibers may also be wet laid as compacted pulp sheets for sale or transport to distant locations.

Relative to pulp sheets made from conventional, uncrosslinked cellulosic fibers, the pulp sheets made from the crosslinked fibers of the present invention are more difficult to compress to conventional pulp sheet densities. Therefore, it may be desirable to combine crosslinked fibers with uncrosslinked fibers, such as those conventionally used in the manufacture of absorbent cores. Pulp sheets containing stiffened, crosslinked fibers preferably contain between about 5% and about 90% uncrosslinked, cellulosic fibers, based upon the total dry weight of the sheet, mixed with the individualized, crosslinked fibers. It is especially preferred to include between about 5% and about 30% of highly refined, uncrosslinked cellulosic fibers, based upon the total dry weight of the sheet. Such highly refined fibers are refined or beaten to a freeness level less than about 300 ml CSF, and preferably less than 100 ml CSF. The uncrosslinked fibers are preferably mixed with an aqueous slurry of the individualized, crosslinked fibers. This mixture may then be formed into a densified pulp sheet for subsequent defibration and formation into absorbent pads. The incorporation of the uncrosslinked fibers eases compression of the pulp sheet into a densified form, while imparting a surprisingly small loss in absorbency to the subsequently formed absorbent pads. The uncrosslinked fibers additionally increase the tensile strength of the pulp sheet and to absorbent pads made either from the pulp sheet or directly from the mixture of crosslinked and uncrosslinked fibers. Regardless of whether the blend of crosslinked and uncrosslinked fibers are first made into a pulp sheet and then formed into an absorbent pad or formed directly into an absorbent pad, the absorbent pad may be air-laid or wet-laid.

Sheets or webs made from the individualized, crosslinked fibers, or from mixtures also containing uncrosslinked fibers, will preferably have basis weights of less than about 800 g/m2 and densities of less than about 0.60 g/cm3. Although it is not intended to limit the scope of the invention, wet-laid sheets having basis weights between 300 g/m2 and about 600 g/m2 and densities between 0.07 g/cm3 and about 0.30 g/cm3 are especially contemplated for direct application as absorbent cores in disposable articles such as diapers, tampons, and other catamenial products. Structures having basis weights and densities higher than these levels are believed to be most useful for subsequent comminution and air-laying or wet-laying to form a lower density and basis weight structure which is more useful for absorbent applications. Furthermore, such higher basis weight and density structures also exhibit surprisingly high absorptivity and responsiveness to wetting. Other applications contemplated for the fibers of the present invention include low density tissue sheets having densities which may be less than about 0.03 g/cc.

If desired, the crosslinked fibers can be further processed to remove excess, unreacted crosslinking agent. One series of treatments found to successfully remove excess crosslinking agent comprise, in sequence, washing the crosslinked fibers, allowing the fibers to soak in an aqueous solution for an appreciable time, screening the fibers, dewatering the fibers, e.g., by centrifuging, to a consistency of between about 40% and about 80%, mechanically defibrating the dewatered fibers as previously described and air drying the fibers. A sufficient amount of an acidic substance may be added to the wash solution, if necessary, to keep the wash solution at a pH of less than about 7. Without being bound by theory, it is believed that the ester crosslinks are not stable under alkaline conditions and that keeping the wash treatment pH in the acidic range inhibits reversion of the ester crosslinks which have formed. Acidity may be introduced by mineral acids such as sulfuric acid, or alternatively in the form of acidic bleach chemicals such as chlorine dioxide and sodium hydrosulfite (which may also be added to brighten the crosslinked fibers). This process has been found to reduce residual free crosslinking agent content to between about 0.01% and about 0.15%.

The crosslinked fibers described herein are useful for a variety of absorbent articles including, but not limited to, tissue sheets, disposable diapers, catamenials, sanitary napkins, tampons, and bandages wherein each of said articles has an absorbent structure containing the individualized, crosslinked fibers described herein. For example, a disposable diaper or similar article having a liquid permeable topsheet, a liquid impermeable backsheet connected to the topsheet, and an absorbent structure containing individualized, crosslinked fibers is particularly contemplated. Such articles are described generally in U.S. Pat. No. 3,860,003, issued to Kenneth B. Buell on Jan. 14, 1975, hereby incorporated by reference into this disclosure. The crosslinked fibers described herein are also useful for making articles such as filter media.

Conventionally, absorbent cores for diapers and catamenials are made from unstiffened, uncrosslinked cellulosic fibers, wherein the absorbent cores have dry densities of about 0.06 g/cc and about 0.12 g/cc. Upon wetting, the absorbent core normally displays a reduction in volume.

It has been found that the crosslinked fibers of the present invention can be used to make absorbent cores having substantially higher fluid absorbing properties including, but not limited to, absorbent capacity and wicking rate relative to equivalent density absorbent cores made from conventional, uncrosslinked fibers or prior known crosslinked fibers. Furthermore, these improved absorbency results may be obtained in conjunction with increased levels of wet resiliency. For absorbent cores having densities of between about 0.05 g/cc and about 0.15 g/cc which maintain substantially constant volume upon wetting, it is especially preferred to utilize crosslinked fibers having crosslinking levels of between about 1.0 weight % and about 10.0 weight % crosslinking agent, based upon a dry cellulose anhydroglucose molar basis. Absorbent cores made from such fibers have a desirable combination of structural integrity, i.e., resistance to compression, and wet resilience. The term wet resilience, in the present context, refers to the ability of a moistened pad to spring back towards its original shape and volume upon exposure to and release from compressional forces. Compared to cores made from untreated fibers, and prior known crosslinked fibers, the absorbent cores made from the fibers of the present invention will regain a substantially higher proportion of their original volumes upon release of wet compressional forces.

In another preferred embodiment, the individualized, crosslinked fibers are formed into either an air laid or wet laid (and subsequently dried) absorbent core which is compressed to a dry density less than the equilibrium wet density of the pad. The equilibrium wet density is the density of the pad, calculated on a dry fiber basis when the pad is fully saturated with fluid. When fibers are formed into an absorbent core having a dry density less than the equilibrium wet density, upon wetting to saturation, the core will collapse to the equilibrium wet density. Alternatively, when fibers are formed into an absorbent core having a dry density greater than the equilibrium wet density, upon wetting to saturation, the core will expand to the equilibrium wet density. Pads made from the fibers of the present invention have equilibrium wet densities which are substantially lower than pads made from conventional fluffed fibers. The fibers of the present invention can be compressed to a density higher than the equilibrium wet density, to form a thin pad which, upon wetting, will expand, thereby increasing absorbent capacity, to a degree significantly greater than obtained for uncrosslinked fibers.

In another preferred embodiment, high absorbency properties, wet resilience, and responsiveness to wetting may be obtained for crosslinking levels of between about 3.0 weight % and about 8.0 weight % crosslinking agent, calculated on a dry fiber weight basis. Preferably, such fibers are formed into absorbent cores having dry densities greater than their equilibrium wet densities. Preferably, the absorbent cores are compressed to densities of between about 0.12 g/cc and about 0.60 g/cc, wherein the corresponding equilibrium wet density is less than the density of the dry compressed pad. Also, preferably the absorbent cores are compressed to a density of between about 0.12 g/cc and about 0.40 g/cc, wherein the corresponding equilibrium wet densities are between about 0.08 g/cc and about 0.12 g/cc, and are less than the densities of the dry, compressed cores. It should be recognized, however, that absorbent structures within the higher density range can be made from crosslinked fibers having higher crosslinking levels, as can lower density absorbent structures be made from crosslinked fibers having lower levels of crosslinking. Improved performance relative to prior known individualized, crosslinked fibers is obtained for all such structures.

While the foregoing discussion involves preferred embodiments for high and low density absorbent structures, it should be recognized that a variety of combinations of absorbent structure densities and crosslinking agent levels between the ranges disclosed herein will provide superior absorbency characteristics and absorbent structure integrity relative to conventional cellulosic fibers and prior known crosslinked fibers. Such embodiments are meant to be included within the scope of this invention.

PROCEDURE FOR DETERMINING FLUID RETENTION VALUE

The following procedure can be utilized to determine the water retention value of cellulosic fibers.

A sample of about 0.3 g to about 0.4 g of fibers is soaked in a covered container with about 100 ml distilled or deionized water at room temperature for between about 15 and about 20 hours. The soaked fibers are collected on a filter and transferred to an 80-mesh wire basket supported about 1½ inches above a 60-mesh screened bottom of a centrifuge tube. The tube is covered with a plastic cover and the sample is centrifuged at a relative centrifuge force of 1500 to 1700 gravities for 19 to 21 minutes. The centrifuged fibers are then removed from the basket and weighed. The weighed fibers are dried to a constant weight at 105° C. and reweighed. The water retention value is calculated as follows:

$$WRV = \frac{(W-D)}{D} \times 100 \tag{1}$$

where,

W=wet weight of the centrifuged fibers;

D=dry weight of the fibers; and

W–D=weight of absorbed water.

PROCEDURE FOR DETERMINING DRIP CAPACITY

The following procedure can be utilized to determine drip capacity of absorbent cores. Drip capacity is utilized as a combined measure of absorbent capacity and absorbency rate of the cores.

A four inch by four inch absorbent pad weighing about 7.5 g is placed on a screen mesh. Synthetic urine is applied to the center of the pad at a rate of 8 ml/s. The flow of synthetic urine is halted when the first drop of synthetic urine escapes from the bottom or sides of the pad. The drip capacity is calculated by the difference in mass of the pad prior to and subsequent to introduction of the synthetic urine divided by the mass of the fibers, bone dry basis.

PROCEDURE FOR DETERMINING WET COMPRESSIBILITY

The following procedure can be utilized to determine wet compressibility of absorbent structures. Wet compressibility is utilized as a measure of resistance to wet compression, wet structural integrity and wet resilience of the absorbent cores.

A four inch by four inch square pad weighing about 7.5 g is prepared, its thickness measured and density calculated. The pad is loaded with synthetic urine to ten times its dry weight or to its saturation point, whichever is less. A 0.1 PSI compressional load is applied to the pad. After about 60 seconds, during which time the pad equilibrates, the thickness of the pad is measured. The compressional load is then increased to 1.1 PSI, the pad is allowed to equilibrate, and the thickness is measured. The compressional load is then reduced to 0.1 PSI, the pad allowed to equilibrate and the thickness is again measured. The densities are calculated for the pad at the original 0.1 PSI load, the 1.1 PSI load and the second 0.1 PSI load, referred to as 0.1 PSIR (PSI rebound) load. The void volume reported in cc/g, is then determined for each respective is pressure load. The void volume is the reciprocal of the wet pad density minus the fiber volume (0.95 cc/g). The 0.1 PSI and 1.1 PSI void volumes are useful indicators of resistance to wet compression and wet structural integrity. Higher void volumes for a common initial pad densities indicate greater resistance to wet compression and greater wet structural integrity. The difference between 0.1 PSI and 0.1 PSIR void volumes is useful for comparing wet resilience of absorbent pads. A smaller difference between 0.1 PSI void volume and 0.1 PSIR void volume, indicates higher wet resilience.

Also, the difference in caliper between the dry pad and the saturated pad prior to compression is found to be a useful indicator of the responsiveness to wetting of the pads.

PROCEDURE FOR DETERMINING DRY COMPRESSIBILITY

The following procedure can be utilized to determine dry compressibility of absorbent cores. Dry compressibility is utilized as a measure of dry resilience of the cores.

A four inch by four inch square air laid pad having a mass of about 7.5 g is prepared and compressed, in a dry state, by a hydraulic press to a pressure of 5500 lbs/16 in². The pad is inverted and the pressing is repeated. The thickness of the pad is measured before and after pressing with a no-load caliper. Density before and after pressing is then calculated as mass/(area X thickness). Larger differences between density before and after pressing indicate lower dry resilience.

PROCEDURE FOR DETERMINING LEVEL OF $C_2$–$C_9$ POLYCARBOXYLIC ACID REACTED WITH CELLULOSIC FIBERS

There exist a variety of analytical methods suitable for determining the level of polycarboxylic acid crosslinked with cellulosic fibers. Any suitable method can be used. For the purposes of determining the level of preferred $C_2$–$C_9$ polycarboxylic acid (i.e., citric acid) which reacts to form intrafiber crosslink bonds with the cellulosic component of the individualized, crosslinked fibers in the examples of the present invention, the following procedure can be used. First, a sample of the crosslinked fibers is washed with sufficient hot water to remove any unreacted crosslinking chemicals or catalysts. Next, the fibers are dried to equilibrium moisture content.

The carboxyl group content of the individualized, crosslinked fibers is then determined essentially in accordance with T.A.P.P.I. Method T 237 OS-77. The crosslinking level of the $C_2$–$C_9$ polycarboxylic acid is then calculated from the fiber's carboxyl group content by the following formula:

Crosslinking level (Weight %) =

$$(C-30) \frac{1 \text{ kg pulp}}{1000 \text{ g pulp}} \cdot \frac{0.001 \text{ eq.}}{\text{meq.}} \cdot \frac{1 \text{ mole carboxylic acid}}{1 \text{ eq. free carboxyl group}} \cdot \frac{192 \text{ g Citric Acid}}{\text{g mole}}$$

Where

C=carboxyl content of crosslinked fibers, meq/kg

30=carboxyl content of uncrosslinked pulp fibers meq/kg

The assumptions made in deriving the above formula are:

1. Two of citric acid's three carboxyl groups react with hydroxyl groups on the cellulose to form a crosslink bond, thus leaving one carboxyl group free to be measured by the carboxyl test.

2. Uncrosslinked pulp fibers have a carboxyl content of 30 meq/kg.

3. No new carboxyl groups are generated on the cellulose during the crosslinking process.

PROCEDURE FOR DETERMINING TWIST COUNT

The following method can be used to determine the twist count of fibers analyzed in this disclosure.

Dry fibers are placed on a slide coated with a thin film of immersion oil, and then covered with a cover slip. The effect of the immersion oil was to render the fiber transparent without inducing swelling and thereby aid in identification of the twist nodes (described below). Wet fibers are placed on a slide by pouring a low consistency slurry of the fibers on the slide which is then covered with a cover slip. The water rendered the fibers transparent so that twist node identification is facilitated.

An image analyzer comprising a computer-controlled microscope, a video camera, a video screen, and a computer loaded with QUIPS software, available from Cambridge Instruments Limited (Cambridge, England; Buffalo, N.Y.), is used to determine twist count.

The total length of fibers within a particular area of the microscope slide at 200× magnification is measured by the image analyzer. The twist nodes are identified and marked by an operator. This procedure is continued, measuring fiber length and marking twist nodes until 1270 mm inches of total fiber length are analyzed. The number of twist nodes per millimeter is calculated from this data by dividing the total fiber length into the total number of twist nodes marked.

PROCEDURE FOR DETERMINING CURL FACTOR

The following method can be utilized to measure fiber curl index.

Dry fibers are placed onto a microscope slide. A cover slip is placed over the fibers and glued in place at the edges. The actual length LA and the maximum projected length LR (equivalent to the length of the longest side of a rectangle encompassing the fiber) are measured utilizing an image analyzer comprising a software controlled microscope, video camera, video monitor, and computer. The software utilized is the same as that described in the Twist Count Image Analysis Method section above.

Once LA and LR are obtained, the curl factor is calculated according to Equation (1) shown above. The curl factor for each sample of fiber is calculated for at least 250 individual fibers and then averaged to determine the mean curl factor for the sample. Fibers having LA less than 0.25 mm are excluded from the calculation.

PROCEDURE FOR MEASURING ODOR COMPOUNDS

The following procedure can be utilized to determine the level of odorous compounds of crosslinked fibers.

A sample of about 1 gram to about 2 grams of material is suspended in 40 ml of water and is homogenized. The aqueous phase is removed by decantation while pressing the solid with a glass rod. The aqueous phase is adjusted to pH 4–4.3, and extracted with 3–4 ml of pentane or by means of a micro liquid/liquid extractor.

Samples are analyzed with a PE 3920 gas chromatograph equipped with an injector/trap, a PID/sniff-port and a mass spectrometer. A Restex $R_{tx}$1 methyl silicone column, 60-m long, 0.32 mm i.d., 1 µm film, is used for the analysis. The temperature is programmed as follows: 4 min isothermal at 50° C., 8° C./min to 280° C., isothermal 16 min.

A chromatogram of a headspace is now obtained and the levels of phenolics and markers of sugar decomposition can be measured.

PROCEDURE FOR DETERMINING ODOR OF CROSSLINKED FIBERS

The proctor (preferably an olfactory professional) will prepare the samples by placing the appropriate amount of each sample in 6 oz. Lily paper cups, then securing a lid on each cup and labeling the cups. When the proctor is ready to evaluate the samples, the lid is removed, 10 cc of cold tap water is added, and then the lid on the cup is replaced. Allow 2 minutes, but not more than 15 minutes, to pass before samples are evaluated. For each three cup set of samples, the panelist will first remove the lid from the identified standard and sniff it. The lid should be placed back onto the cup. The procedure is then followed in turn with each of the remaining samples. The panelists identifies the sample and marks its code on the grading sheet and checks the grade which best describes the overall odor of the sample. Evaluations must be made only by those qualified.

PROCEDURE FOR MEASURING BRIGHTNESS

The following procedure can be utilized to determine the level of brightness: A standard Technidyne TB-1 brightness meter is used. A 4 inch×4 inch air laid pad should be formed using industry standard method. The brightness is then measured on top in the center of the sample.

PROCEDURE FOR MEASURING pH

The following procedure can be utilized to determine the final fiber pH: One gram of crosslinked fiber is added to 100 ml of water. The sample is stirred for 60 minutes and the pH is recorded.

The following examples illustrate the practice of the present invention but are not intended to be limiting thereof.

EXAMPLE I

Reduced odor individualized, crosslinked fibers are made by a dry crosslinking process utilizing citric acid as the crosslinking agent, sodium hydroxide and hydrogen peroxide to reduce odor and improve brightness. The procedure used to produce the reduced odor, citric acid crosslinked fibers is as follows:

1. For each sample, 1735 g of once dried, southern softwood kraft (SSK) pulp is provided in sheet form. The fibers have a moisture content of about 7% (equivalent to 93% consistency).
2. The pulp sheet is contacted with 8% citric acid and 1% sodium hypophosphite. The pH is adjusted to 2.5 with sodium hydroxide. The consistency of the resulting pulpsheet and chemicals is 60%.
3. Next, the fibers are defibrated using a Sprout-Waldron 12" disk refiner (model number 105-A) whose plates are set at a gap which yields fibers substantially individualized but with a minimum amount of fiber damage. As the individualized fibers exit the refiner, they are flash dried with hot air in two vertical tubes in order to provide fiber twist and curl. The fibers contain approximately 10% moisture upon exiting these tubes and are ready to be cured. If the moisture content of the fibers is greater than about 10% upon exiting the flash drying tubes, then the fibers are dried with ambient temperature air until the moisture content is about 10%.
4. The nearly dry fibers are then placed on trays and cured in an air-through drying oven for a length of time and at a temperature which in practice depends on the amount of citric acid added, dryness of the fibers, etc. In this example, the samples are cured at a temperature of about 330° C. for a period of about 5 minutes. Crosslinking is completed during the period in the oven.

5. The crosslinked individualized fibers are then contacted with a water solution containing 0.25% sodium hydroxide and 0.13% hydrogen peroxide, and well mixed. The resulting fibers contain 10% moisture.

6. The odor is zero, final pH is 6.0 and the resulting brightness is 84. The material has reduced levels of sugar decomposition markers (5–7×) and anhydrides of citric acid (2–3×).

The resulting individualized crosslinked cellulosic fibers have a WRV of 37.6 and contain 3.5 weight % citric acid, calculated on a dry fiber weight basis, reacted with the fibers in the form of intrafiber crosslink bonds. The final odor is zero, the resulting brightness is 84, and the final pH is 6.2.

Importantly, the resulting individualized, crosslinked fibers have reduced odor, higher brightness, improved responsiveness to wetting relative to conventional, uncrosslinked fibers and prior known crosslinked fibers, and can be safely utilized in the vicinity of human skin.

EXAMPLE II

Reduced odor individualized, crosslinked fibers are made by a dry crosslinking process utilizing citric acid as the crosslinking agent, sodium hydroxide and hydrogen peroxide to reduce odor and improve brightness. The procedure used to produce the reduced odor, citric acid crosslinked fibers is as follows:

1. For each sample, 1735 g of once dried, southern softwood kraft (SSK) pulp is provided in sheet form. The fibers have a moisture content of about 7% (equivalent to 93% consistency).

2. The pulp sheet is contacted with 8% citric acid and 1% sodium hypophosphite. The pH is adjusted to 2.5 with sodium hydroxide. The consistency of the resulting pulpsheet and chemicals is 60%.

3. Next, the fibers are defibrated using a Sprout-Waldron 12" disk refiner (model number 105-A) whose plates are set at a gap which yields fibers substantially individualized but with a minimum amount of fiber damage. As the individualized fibers exit the refiner, they are flash dried with hot air in two vertical tubes in order to provide fiber twist and curl. The fibers contain approximately 10% moisture upon exiting these tubes and are ready to be cured. If the moisture content of the fibers is greater than about 10% upon exiting the flash drying tubes, then the fibers are dried with ambient temperature air until the moisture content is about 10%.

4. The nearly dry fibers are then placed on trays and cured in an air-through drying oven for a length of time and at a temperature which in practice depends on the amount of citric acid added, dryness of the fibers, etc. In this example, the samples are cured at a temperature of about 330° C. for a period of about 5 minutes. Crosslinking is completed during the period in the oven.

5. The crosslinked individualized fibers are then contacted with a water solution containing 0.09 weight % sodium hydroxide and 0.02% hydrogen peroxide. The resulting fibers contain 10% moisture.

The resulting individualized crosslinked cellulosic fibers have a WRV of 37.6 and contain 3.5 weight % citric acid, calculated on a dry fiber weight basis, reacted with the fibers in the form of intrafiber crosslink bonds. The final odor is zero, the resulting brightness is 84, and the final pH is 6.2.

Importantly, the resulting individualized, crosslinked fibers have reduced odor, higher brightness, improved responsiveness to wetting relative to conventional, uncrosslinked fibers and prior known crosslinked fibers, and can be safely utilized in the vicinity of human skin.

EXAMPLE III

Reduced odor individualized, crosslinked fibers are made by a dry crosslinking process utilizing citric acid as the crosslinking agent, sodium hydroxide and hydrogen peroxide to reduce odor and improve brightness. The procedure used to produce the reduced odor, citric acid crosslinked fibers is as follows:

1. For each sample, 1735 g of once dried, southern softwood kraft (SSK) pulp is provided in sheet form. The fibers have a moisture content of about 7% (equivalent to 93% consistency).

2. The pulp sheet is contacted with 8% citric acid and 1% sodium hypophosphite. The pH is adjusted to 2.5 with sodium hydroxide. The consistency of the resulting pulpsheet and chemicals is 60%.

3. Next, the fibers are defibrated using a Sprout-Waldron 12" disk refiner (model number 105-A) whose plates are set at a gap which yields fibers substantially individualized but with a minimum amount of fiber damage. As the individualized fibers exit the refiner, they are flash dried with hot air in two vertical tubes in order to provide fiber twist and curl. The fibers contain approximately 10% moisture upon exiting these tubes and are ready to be cured. If the moisture content of the fibers is greater than about 10% upon exiting the flash drying tubes, then the fibers are dried with ambient temperature air until the moisture content is about 10%.

4. The nearly dry fibers are then placed on trays and cured in an air-through drying oven for a length of time and at a temperature which in practice depends on the amount of citric acid added, dryness of the fibers, etc. In this example, the samples are cured at a temperature of about 330° C. for a period of about 5 minutes. Crosslinking is completed during the period in the oven.

5. The crosslinked individualized fibers are then contacted with a water solution containing 0.16% sodium hydroxide and 0.1% hydrogen peroxide. The resulting fibers contain 10% moisture.

The resulting individualized crosslinked cellulosic fibers have a WRV of 37.6 and contain 3.5 weight % citric acid reacted with the fibers in the form of intrafiber crosslink bonds.

The final odor is zero, the resulting brightness is 82 and the final pH is 6.4.

Importantly, the resulting individualized, crosslinked fibers have reduced odor, higher brightness, improved responsiveness to wetting relative to conventional, uncrosslinked fibers and prior known crosslinked fibers, and can be safely utilized in the vicinity of human skin.

What is claimed is:

1. A process for preparing reduced odor, individualized, polycarboxylic acid crosslinked cellulosic fibers, said process comprising the steps of:

a. providing cellulosic fibers;

b. contacting said fibers with a solution containing an effective amount of a $C_2$–$C_9$ polycarboxylic acid crosslinking agent, wherein said $C_2$–$C_9$ polycarboxylic acid crosslinking agent is selected from the group consisting of:
  (i) aliphatic and alicyclic $C_2$–$C_9$ polycarboxylic acids either olefinically saturated or unsaturated and having at least three carboxyl groups per molecule; and
  (ii) aliphatic and alicyclic $C_2$–$C_9$ polycarboxylic acids having two carboxyl groups per molecule and having a carbon—carbon double bond located alpha, beta to one or both of the carboxyl groups,
  wherein one carboxyl group in said $C_2$–$C_9$ polycarboxylic acid crosslinking agent is separated from a second carboxyl group by either two or three carbon atoms,
c. mechanically separating said fibers into substantially individual form;
d. drying said fibers and reacting said crosslinking agent with said fibers to form crosslink bonds while said fibers are in substantially individual form, to form intrafiber crosslink bonds, wherein said crosslinked fibers have a pH less than 5; and
e. raising the pH of the crosslinked fibers to at least 5 by contacting said crosslinked fibers with an alkaline solution.

2. The process of claim 1, wherein the step (e) of raising the pH of the crosslinked fibers to at least 5 further comprises contacting said crosslinked fibers with an oxidizing bleaching agent.

3. The process of claim 2 wherein said alkaline solution has a pH greater than about 9.

4. The process of claim 3 wherein said alkaline solution comprises an aqueous medium and an alkaline compound selected from the group consisting of sodium hydroxide, sodium hypochlorite, sodium bisulfite, ammonium hydroxide, and mixtures thereof.

5. The process of claim 4 wherein said alkaline solution comprises an aqueous medium and sodium hydroxide.

6. The process of claim 4 wherein the oxidizing bleaching agent is selected from the group consisting of hydrogen peroxide, sodium peroxide, peracetic acid, chlorine dioxide, sodium hypochlorite, hydrogen chloride, and mixtures thereof.

7. The process of claim 6 wherein said oxidizing bleaching agent is hydrogen peroxide.

8. The process of claim 7 wherein said alkaline solution comprises an aqueous medium and sodium hydroxide.

9. The process of claim 2 wherein said cellulosic fibers of step (a) have been at least partially bleached.

10. The process of claim 2 wherein said crosslinking agent is selected from the group consisting of citric acid, 1,2,3,4-butane tetracarboxylic acid, and 1,2,3-propane tricarboxylic acid.

11. The process of claim 10 wherein said crosslinking agent is citric acid.

12. The process of claim 10 wherein between about 1.0 weight % and about 10.0 weight % crosslinking agent, based on the dry fiber weight of the cellulosic fibers, reacts with said fibers to form said intrafiber crosslink bonds.

13. The process of claim 12 wherein between about 3.0 weight % and about 8.0 weight % crosslinking agent, based on the dry fiber weight of the cellulosic fibers, reacts with said fibers to form said intrafiber crosslink bonds.

14. The process of claim 12 wherein said crosslinking agent is reacted with said fibers to form intrafiber crosslink bonds in the presence of at least one catalyst selected from the group consisting of alkali metal hypophosphites, alkali metal phosphites, alkali metal polyphosphates, alkali metal phosphates, and alkali metal sulfates.

15. The process of claim 14 wherein said catalyst is an alkali metal hypophosphite.

16. The process of claim 14 wherein said crosslinking agent is citric acid.

17. The process of claim 12 wherein the water retention values of said crosslinked cellulosic fibers is from about 25 to 60.

18. The process of claim 17 wherein the water retention values of said crosslinked cellulosic fibers is from about 30 to about 45.

19. The process of claim 2 wherein said crosslinking agent is selected from the group consisting of oxydisuccinic acid, tartrate monosuccinic acid having the formula:

$$\underset{COOH}{HOCH}-\underset{COOH}{CH}-O-\underset{COOH}{CH}-\underset{COOH}{CH_2}$$

and tartrate disuccinic acid having the formula:

$$\underset{COOH}{CH_2}-\underset{COOH}{CH}-O-\underset{COOH}{CH}-\underset{COOH}{CH}-O-\underset{COOH}{CH}-\underset{COOH}{CH_2}$$

20. The process of claim 19 wherein said crosslinking agent is oxydisuccinic acid.

21. The process of claim 2 wherein the pH of the crosslinked fibers after being contacted with said alkaline solution in step (e) is from 5.5 to 6.5.

* * * * *

UNITED STATES PATENT AND TRADEMARK OFFICE
CERTIFICATE OF CORRECTION

PATENT NO. : 5,562,740
DATED : October 8, 1996
INVENTOR(S) : Jeffery T. Cook et al.

It is certified that error appears in the above-indentified patent and that said Letters Patent is hereby corrected as shown below:

Cover page, Item [75] Inventors, after Jeffrey T. Cook, "Cincinatti;" should read-- Cincinnati; --.

Cover page, Item [73] Assignee, "Cincinatti," should read -- Cincinnati, --.

Cover page, Item [73] Assignee, add name of co-assignee -- The Weyerhaeuser Company, Tacoma, Washington --.

Column 19, line 59, "respective is" should read -- respective --.

Signed and Sealed this

Twenty-third Day of November, 1999

Attest:

Q. TODD DICKINSON

*Attesting Officer*     *Acting Commissioner of Patents and Trademarks*